United States Patent
Gatzerneyer et al.

(10) Patent No.: US 7,418,757 B2
(45) Date of Patent: Sep. 2, 2008

(54) MUSICAL TOOTHBRUSH

(75) Inventors: John J. Gatzerneyer, Hillsborough, NJ (US); Eduardo J. Jimenez, Manalapan, NJ (US); Evan Ward, Chicago, IL (US); Jim Michaels, Downers Grove, IL (US)

(73) Assignee: Colgate-Palmolive Company, New York, NY (US)

( * ) Notice: Subject to any disclaimer, the term of this patent is extended or adjusted under 35 U.S.C. 154(b) by 107 days.

(21) Appl. No.: 11/413,624

(22) Filed: Apr. 28, 2006

(65) Prior Publication Data

US 2007/0094822 A1 May 3, 2007

Related U.S. Application Data

(60) Provisional application No. 60/738,528, filed on Nov. 21, 2005, provisional application No. 60/677,192, filed on May 3, 2005.

(51) Int. Cl.
*A46B 15/00* (2006.01)
(52) U.S. Cl. .................................. 15/105; 15/167.1
(58) Field of Classification Search .............. 15/105, 15/167.1, 22.1, 176.1
See application file for complete search history.

(56) References Cited

U.S. PATENT DOCUMENTS

| | | | |
|---|---|---|---|
| 1,986,955 A | 1/1935 | Bedell | |
| 3,027,507 A | 3/1962 | Hübner | |
| 3,458,794 A | 7/1969 | Bohnstedt | |
| 4,075,458 A | 2/1978 | Moyer | |
| 4,341,230 A | 7/1982 | Siahou | |
| 4,698,869 A * | 10/1987 | Mierau et al. | 15/22.1 |
| 4,716,614 A * | 1/1988 | Jones et al. | 15/105 |
| 4,744,124 A | 5/1988 | Wang | |
| 4,764,961 A | 8/1988 | Hung | |
| 4,788,734 A | 12/1988 | Bauer | |
| 4,866,807 A | 9/1989 | Kreit et al. | |
| 4,944,016 A | 7/1990 | Christian | |
| 4,944,704 A | 7/1990 | Grace | |
| 5,006,779 A | 4/1991 | Fenne | |
| 5,044,037 A | 9/1991 | Brown | |
| 5,133,102 A | 7/1992 | Sakuma | |
| 5,165,131 A | 11/1992 | Staar | |
| D340,455 S | 10/1993 | Christian | |
| 5,259,086 A | 11/1993 | Fong | |
| 5,335,798 A | 8/1994 | Bonwell | |
| 5,337,435 A | 8/1994 | Krasner | |
| 5,438,726 A | 8/1995 | Leite | |
| 5,572,762 A | 11/1996 | Scheiner | |
| 5,628,641 A | 5/1997 | Hahn | |

(Continued)

FOREIGN PATENT DOCUMENTS

DE    31 49 233    4/1983

(Continued)

*Primary Examiner*—David B Thomas
(74) *Attorney, Agent, or Firm*—Michael J. Wallace, Jr.

(57) ABSTRACT

A toothbrush assembly comprises a toothbrush, a storage unit comprising an input, a memory for storing audio signals received via the input, and an output for transmitting or playing the stored audio signals. A variety of different embodiments of storage unit and toothbrush configurations are described, each creating an environment that makes tooth brushing enjoyable so that children and teenagers in particular will brush as often as they should and for the recommended period of time

46 Claims, 12 Drawing Sheets

U.S. PATENT DOCUMENTS

| | | | |
|---|---|---|---|
| 5,786,749 | A | 7/1998 | Johnson |
| 5,810,601 | A | 9/1998 | Williams |
| 5,864,288 | A | 1/1999 | Hogan |
| 5,924,159 | A | 7/1999 | Haitin |
| 5,960,507 | A | 10/1999 | Dutra |
| 6,029,303 | A | 2/2000 | Dewan |
| 6,115,477 | A | 9/2000 | Filo |
| 6,154,912 | A | 12/2000 | Li |
| 6,199,239 | B1 | 3/2001 | Dickerson |
| 6,202,245 | B1 | 3/2001 | Khodadadi |
| 6,325,066 | B1 | 12/2001 | Hughes |
| 6,389,633 | B1 | 5/2002 | Rosen |
| 6,397,424 | B1 | 6/2002 | Leung |
| 6,536,068 | B1 | 3/2003 | Yang |
| 6,554,619 | B2 | 4/2003 | Williams |
| 6,611,780 | B2 | 8/2003 | Lundell |
| 6,619,969 | B2 | 9/2003 | Scheider |
| 6,633,747 | B1 | 10/2003 | Reiss |
| 6,648,641 | B1 | 11/2003 | Viltro |
| 6,658,687 | B1 | 12/2003 | McDonald |
| 6,923,409 | B2 * | 8/2005 | Strunk ........................ 248/111 |
| 7,013,522 | B2 | 3/2006 | Kumagai |
| 2001/0004428 | A1 | 6/2001 | Horng |
| 2002/0067084 | A1 | 6/2002 | Jung |
| 2003/0017874 | A1 | 1/2003 | Jianfei |
| 2003/0232303 | A1 | 12/2003 | Black |
| 2004/0000017 | A1 | 1/2004 | Kumagai |
| 2004/0255409 | A1 | 12/2004 | Hilscher |
| 2005/0066461 | A1 | 3/2005 | Chang |
| 2005/0152231 | A1 | 7/2005 | Yeh |
| 2005/0172433 | A1 | 8/2005 | Oliver |
| 2005/0278882 | A1 | 12/2005 | Drzewiecki et al. |
| 2006/0037158 | A1 * | 2/2006 | Foley et al. ................... 15/105 |

FOREIGN PATENT DOCUMENTS

| | | |
|---|---|---|
| DE | 3149233 A1 * | 4/1983 |
| EP | 0435329 | 7/1991 |
| JP | 01008914 | 1/1989 |
| JP | 2003/180717 | 7/2003 |
| JP | 2004/065838 | 3/2004 |
| JP | 2004/105246 | 4/2004 |
| WO | WO 98/55274 | 12/1998 |
| WO | WO 99/32011 | 7/1999 |
| WO | WO 00/74591 | 12/2000 |
| WO | WO 2004/026077 | 4/2004 |
| WO | WO 2004/098445 | 11/2004 |
| WO | WO 2006/002101 | 1/2006 |

* cited by examiner

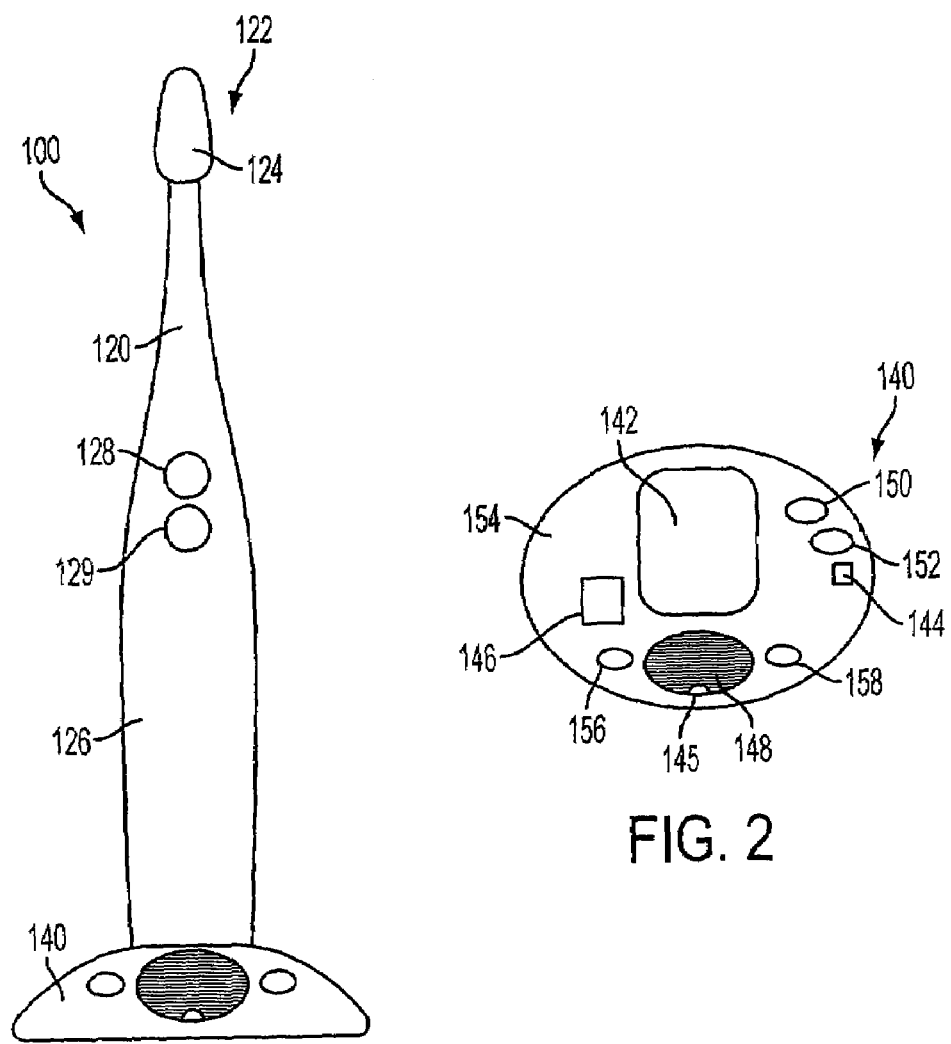
FIG. 1
FIG. 2
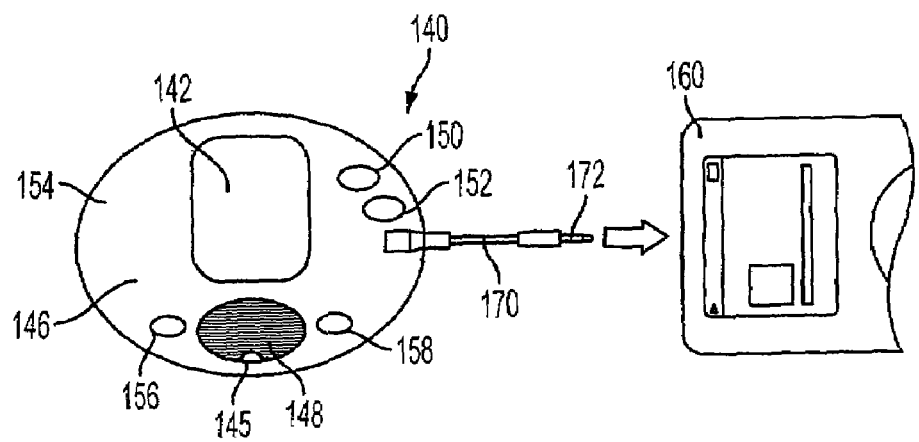
FIG. 3

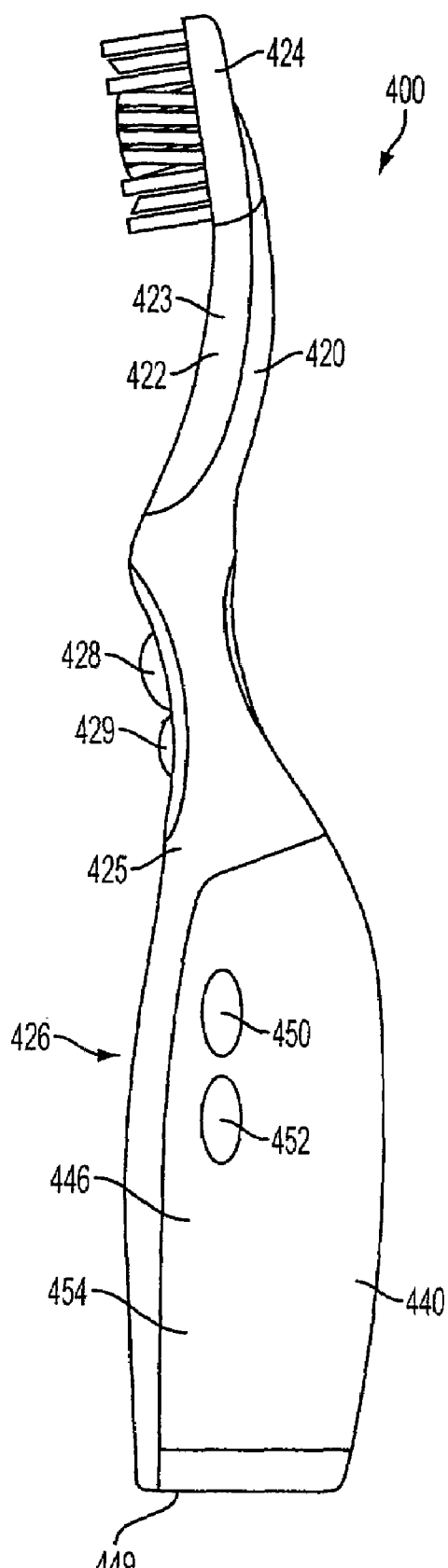
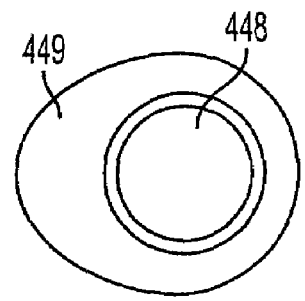
FIG. 10
FIG. 9

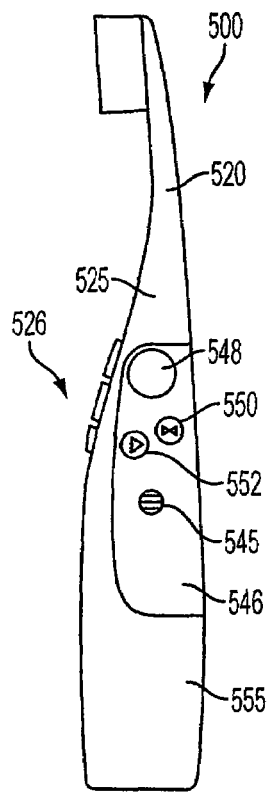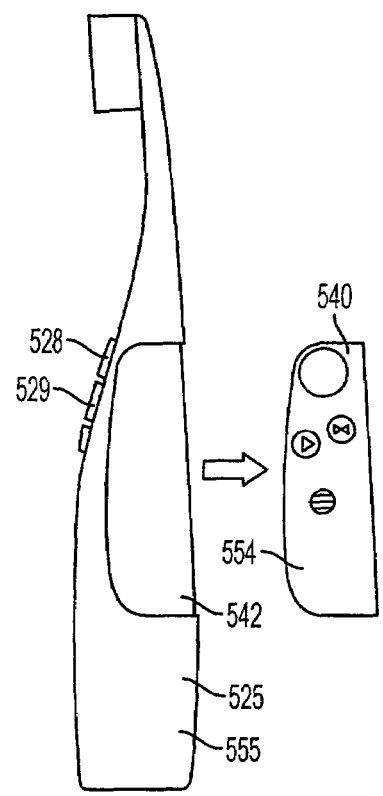
FIG. 13  FIG. 14
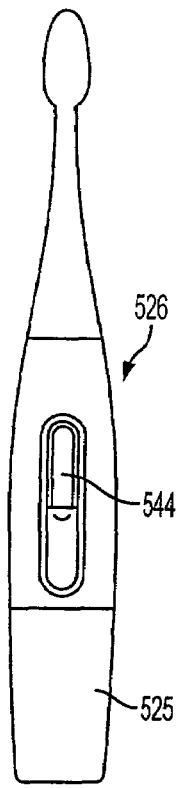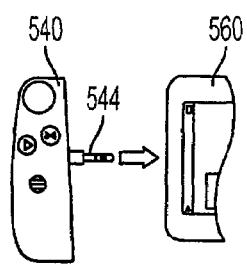
FIG. 15  FIG. 16

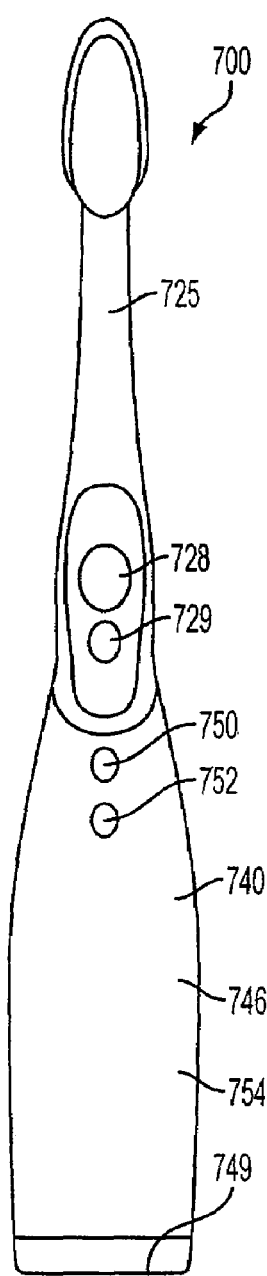
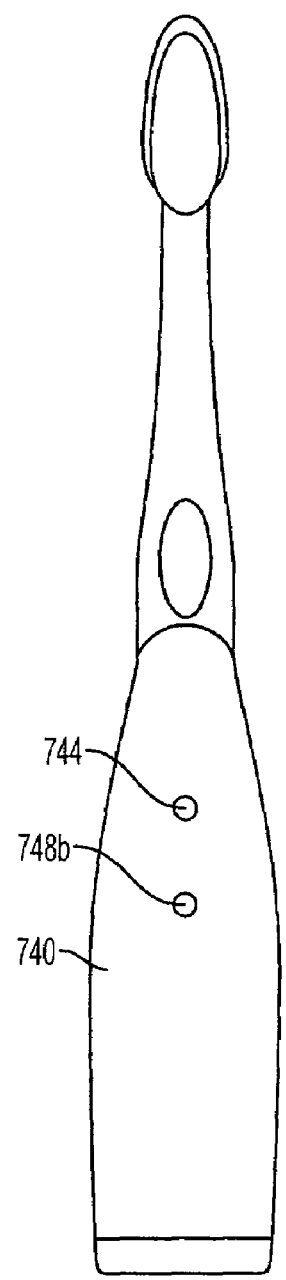
FIG. 18
FIG. 19
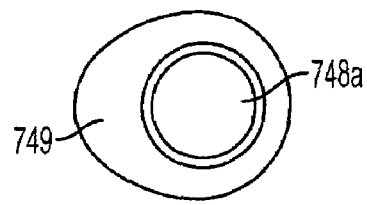
FIG. 20

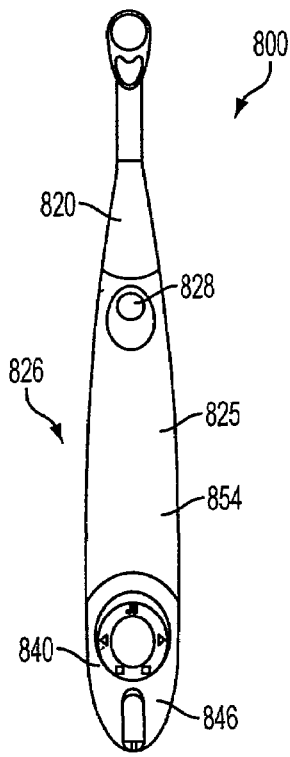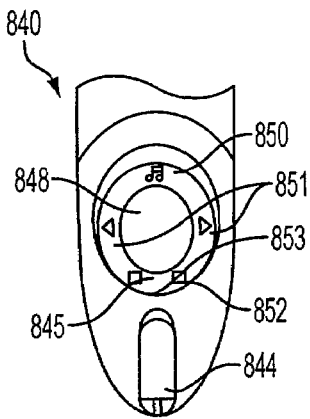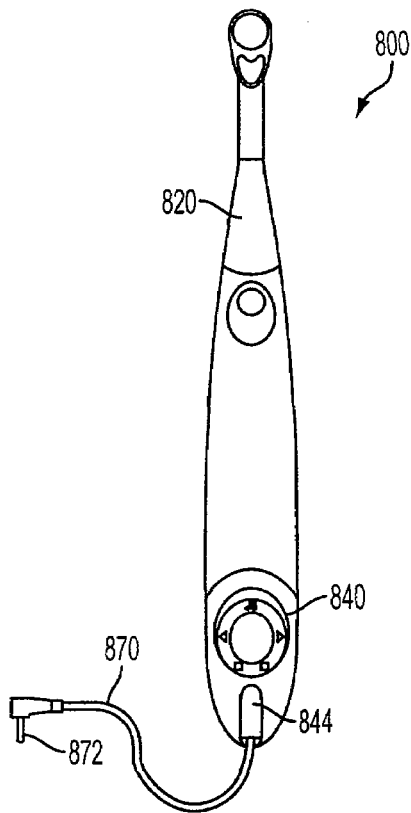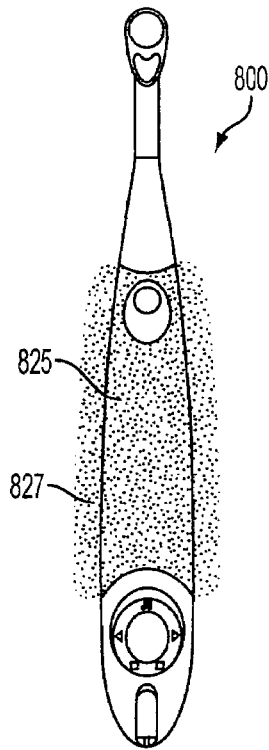
FIG. 22
FIG. 23
FIG. 24
FIG. 25

US 7,418,757 B2

MUSICAL TOOTHBRUSH

CROSS-REFERENCE TO RELATED APPLICATIONS

This application claims the benefit under 35 U.S.C. §119 (e) of U.S. application Ser. No. 60/738,528 filed Nov. 21, 2005, and Ser. No. 60/677,192, filed May 3, 2005, both of which are incorporated by reference herein.

FIELD OF THE INVENTION

The present invention relates to toothbrushes in general, and more particularly to a toothbrush that can record and/or play music or other audio signals.

BACKGROUND OF THE INVENTION

Statistics show that a small percentage of the population in any country brushes one's teeth for the dentist recommended time of two minutes. This can be especially true of younger children and teenagers. Also, tooth brushing is seen as a mundane duty with few pleasurable aspects. Accordingly, there is a need to create an environment that makes tooth brushing enjoyable so that children and teenagers in particular will brush as often as they should and for the recommended period of time.

SUMMARY OF THE INVENTION

The present invention enables a person to know that he/she has brushed one's teeth for a period of time close to the professional recommendation while enjoying a musical interlude of one's choosing. A toothbrush assembly is provided that comprises a toothbrush, a storage unit comprising an input, a memory for storing audio signals received via the input, and an output for transmitting or playing the stored audio signals. A variety of different embodiments of storage unit and toothbrush configurations are discussed herein, each creating an environment that makes tooth brushing enjoyable so that children and teenagers in particular will brush as often as they should and for the recommended period of time.

BRIEF DESCRIPTION OF THE DRAWINGS

FIG. 1 illustrates one embodiment of a toothbrush assembly of the invention.

FIG. 2 illustrates a base of the assembly of FIG. 1.

FIG. 3 illustrates the connection of the base of FIG. 2 to a signal source.

FIG. 9 illustrates an alternative embodiment of a toothbrush assembly.

FIG. 10 illustrates the bottom surface of the assembly of FIG. 9.

FIG. 13 illustrates an alternative embodiment of a toothbrush assembly.

FIG. 14 is an exploded view of the assembly of FIG. 13.

FIG. 15 is a side view of the assembly of FIG. 13.

FIG. 16 illustrates the connection of the storage unit of the assembly of FIG. 13 to a signal source.

FIG. 18 is a front view of an alternative embodiment of a toothbrush assembly of the invention.

FIG. 19 is a rear view of the assembly of FIG. 18.

FIG. 20 illustrates the bottom surface of the assembly of FIG. 18.

FIG. 22 illustrates an alternative embodiment of a toothbrush assembly.

FIG. 23 illustrates the connection of the assembly of FIG. 22 to a signal source (not shown).

FIG. 24 illustrates the storage unit of the assembly of FIG. 22.

FIG. 25 illustrates an embodiment of the assembly of FIG. 22.

DETAILED DESCRIPTION OF THE PREFERRED EMBODIMENTS

Figure 4:
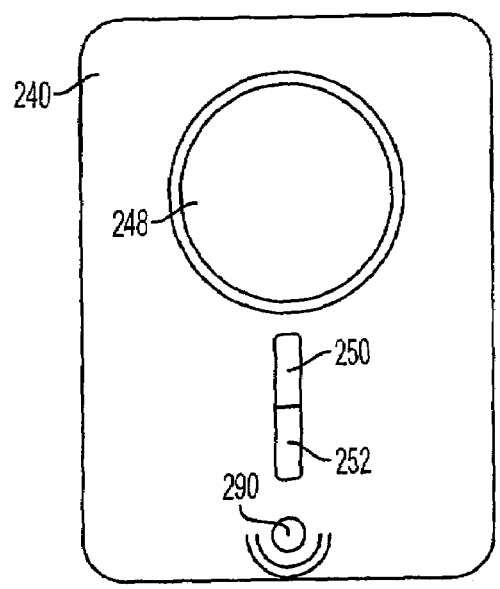
FIG. 4 illustrates a base of an alternative embodiment of an assembly.

The following detailed description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

FIGS. 1-3 illustrate a first embodiment of a toothbrush assembly 100 of the present invention comprising a toothbrush 120 and a base 140. The toothbrush 120 further comprises a head 122 having cleaning elements 124, and a handle 126. The cleaning elements 124 further comprise any known cleaning elements used in toothbrushes or other oral care implements, such as, but not limited to nylon bristles, tufts of bristles, bristle walls, elastomeric elements, and the like. The toothbrush 120 can be a power toothbrush including a power source (not shown) that drives a powered element, such as movable cleaning elements 124 with an activation or "on" button 128 and a deactivation or "off" button 129. Alternatively, the toothbrush 120 can be a manual toothbrush that does not include a power source or a powered element, but is merely retained in the base 140.

The base 140 further comprises a seat 142 for receiving and storing the handle 126 of the toothbrush 120, an input 144 for connection to an audio device 160, a memory 146 (shown graphically in FIG. 2 as a box) for storing audio signals received via the input 144, and an output 148 in the form of a speaker for transmitting the stored audio signals to the user's surroundings. The base 140 further comprises a record button 150 for recording audio signals to the memory 146, and a play button 152 for playing the recorded audio signals through the speaker 148. Also provided are timed playback buttons 156 and 158 for controlling the time of the playback, and a microphone 145 for recording ambient sound directly to the memory 146. A power source 154, such as a battery or the like, is provided in the base 140 to power the record and playback features. Alternatively, the base may plug into a household outlet using a supplied cable connection (not shown).

Music or other audio signals are transferred from the signal source 160 to the base 140 by a wired connection or cable 170 through the use of, for example, a standard headphone jack 172 (i.e. 2.5 mm). The user connects cable 170, which may be stored in the base 140, to the signal source 160 (here shown as an Apple® iPod® for example) and activates the signal transfer from the source 160 to the memory 146 using the play button on the signal source (not shown) and the record button 150. The record button 150 may be depressed once to record a certain period of music, such as three minutes for example, or it may be held down for a period of time equal to the amount of music transferred. The user then activates a timed playback of the stored music through the speaker 148 by pressing one of buttons 156 or 158 to play music for, for example, two minutes upon pressing button 156, or three minutes upon pressing button 158. Other durations may be set, which can correlate with a time period other than two or three minutes, or it can designate a specific number of songs. Alternatively, the user could simply press the play button 152 if a timed playback is not desired. Of course, while any type of musical or non-musical audio signals can be stored in the memory, it is preferred if the audio signals are pleasurable to the user so that the user brushes for the entire playback duration.

Figure 27:
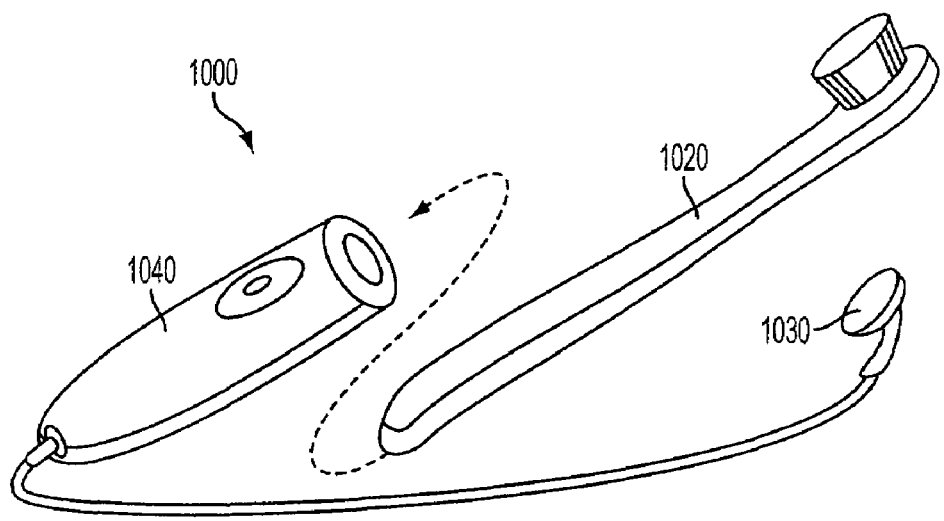
FIG. 27 illustrates an alternative embodiment of an assembly.

For children and teens, the audio signals may comprise a popular musical segment from the radio or the user's audio collection, while for older adults the audio signals may comprise an information-based news summary or stock reports for example that are automatically downloaded from the Internet. Thus, while the assembly 100 of FIGS. 1-3 illustrates a self-contained system, the assembly can be connected to a computer or to the Internet or the like, for automated downloads of audio signals that are retrievable on demand. In addition, the assembly 100 could be used without connecting to an external source. For example, a user can record a to-do list the night before using the microphone input 145, which is played back the next morning using the play button 152. Furthermore, it will be understood that any type of signal, such as audio and/or video, can be stored in the memory 146 of the assembly 100, as long as the assembly 100 includes an appropriate output to present such signal to a user. In other words, the assembly 100 could also include a display screen (not shown) to display video signals stored in the base 140. In another example shown in FIG. 27, an assembly 1000 is comprised of any commercially-available conventional manual or powered toothbrush 1020 and a sleeve-like holder 1040 that includes memory, input, and output audio capabilities and an earpiece 1030 for listening to audio stored in the holder 1040. The holder 1040 of FIG. 27 represents a retrofit-type device that accommodates the handle of an existing toothbrush 1020 and doubles as a supplementary grip when the handle is received in the holder 1040.

In the embodiments to follow, the basic operation of recording and/or storing audio signals, such as music, in a storage unit, for future playback is consistent with the embodiment of FIGS. 1-3. Furthermore, the described signal source could be any local or remote source as long as the signals are capable of being communicated and transferred from the source to the toothbrush assembly. Thus, the connection between the storage unit and the signal source does not have to be a direct physical connection, but could be a wireless connection that utilizes, for example, Bluetooth® technology or the like. The described embodiments illustrate different executions that each creates an environment that makes brushing enjoyable and more likely to be maintained for at least the dentist-recommended period of time.

Figure 5:
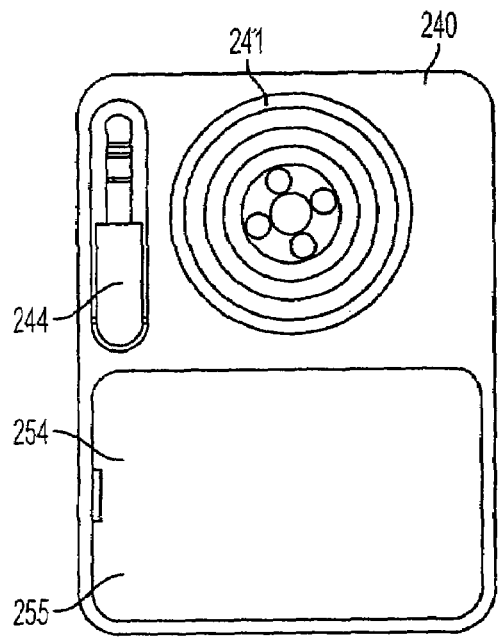
FIG. 5 is a rear view of the base of FIG. 4.
Figure 6:
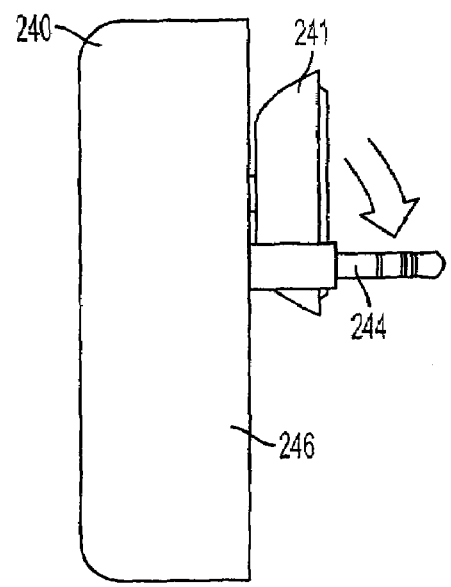
FIG. 6 is a side view of the base of FIG. 4 with the input in an extended condition.

FIGS. 4-6 illustrate an alternative embodiment of a toothbrush assembly base 240, usable with a toothbrush of FIGS. 1-3, for example, that is mountable to a vertical surface by an attachment such as a locking suction cup 241 or the like. Other methods of removable attachment are contemplated. The base 240 further comprises an input 244 for connection to an audio device (not shown), a memory 246 for storing audio signals received via the input 244, and an output 248 in the form of a recessed area speaker for transmitting the stored audio signals to the user's surroundings. The front surface of the base 240 further comprises a record button 250 for recording audio signals to the memory 246, and a play button 252 for playing the recorded audio signals through the speaker 248. The play feature may incorporate a timed playback feature as discussed above. A power source 254, such as a battery or the like, is accessible via an access or a door 255 provided on a rear surface of the base 240, to power the record and playback features. Alternatively, the base may plug into a direct current outlet using a supplied cable connection (not shown). Also provided is a wireless means 290 for communicating with a toothbrush (not shown) as will be described below.

Music or other audio signals are transferred from a signal source (not shown) to the base 240 by a direct connection with the input 244, which in the embodiment of FIGS. 4-6 is a flip-out jack that is movable from a first, storage position recessed within the rear surface of the base 240 as shown in FIG. 5, to a second position extending outwardly from the base 240 as shown by the arrow in FIG. 6. The recessed storage position shown in FIG. 5 prevents the input 244 from interfering with the vertically-oriented attachment of the base 240. The outward extension of the input 244 allows the base 240 to be directly connected or attached to an audio source, such as shown in FIG. 3, for the transfer of audio signals to the memory 246 of the base 240, after which the base 240 may be affixed to a bathroom mirror or wall or the like. The record and play buttons 250, 252 function in a similar manner as described before. Thus, the base 240 may be conveniently connected to a signal source at any location, and then applied to a bathroom mirror for example, for enjoyable playback during brushing. Of course, as the base 240 is effectively self-contained, it may be used in any environment and not necessary restricted to a bathroom or with a tooth brushing activity.

Figure 7:
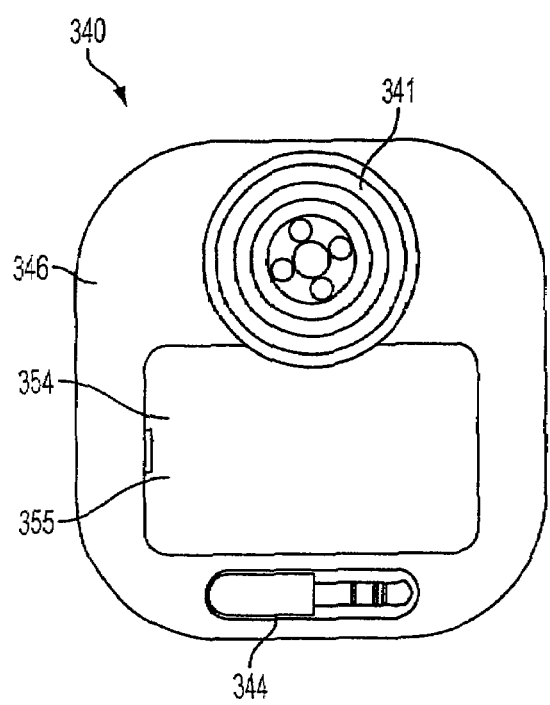
FIG. 7 is a rear view of a base of an alternative embodiment of an assembly of the invention.
Figure 8:
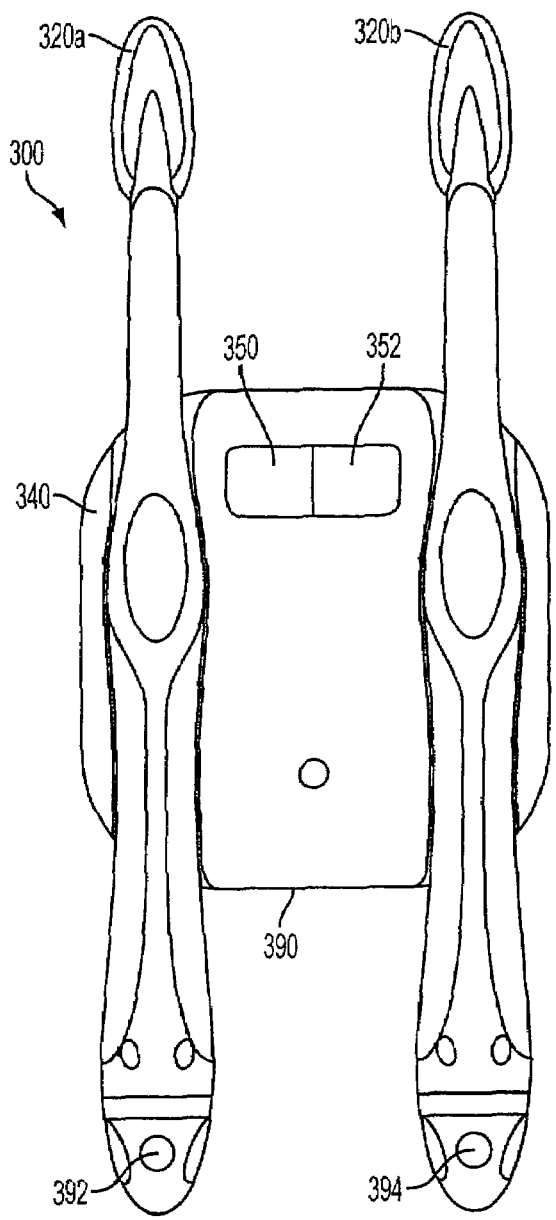
FIG. 8 illustrates an alternative embodiment of an assembly including the base of FIG. 7.
Figure 8B:
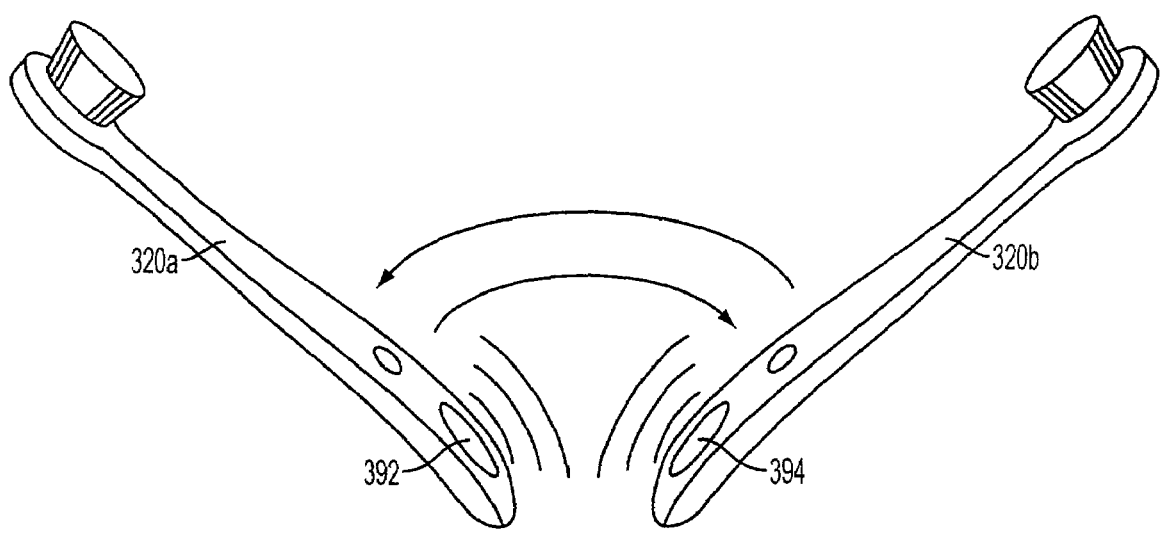
FIG. 8B illustrates communication between toothbrushes depicted in FIGS. 7-8A.
Figure 11:
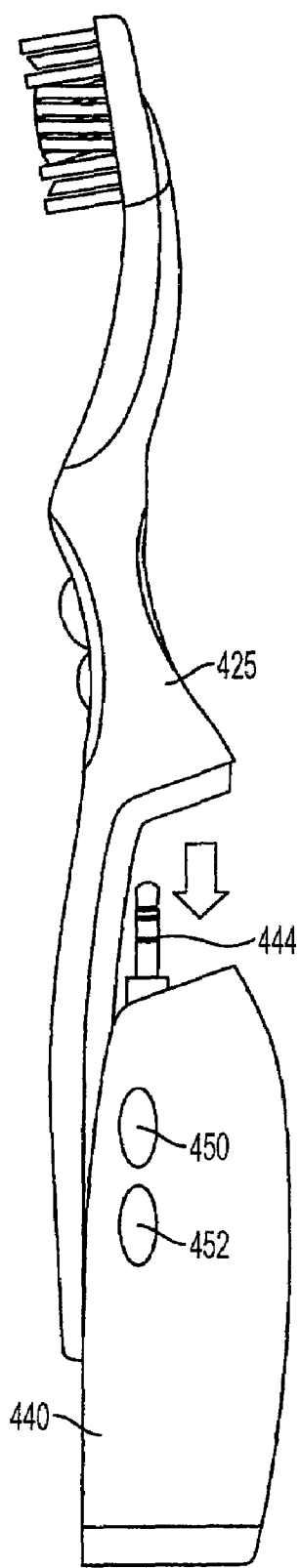
FIG. 11 is an exploded view of the assembly of FIG. 9.
Figure 12:
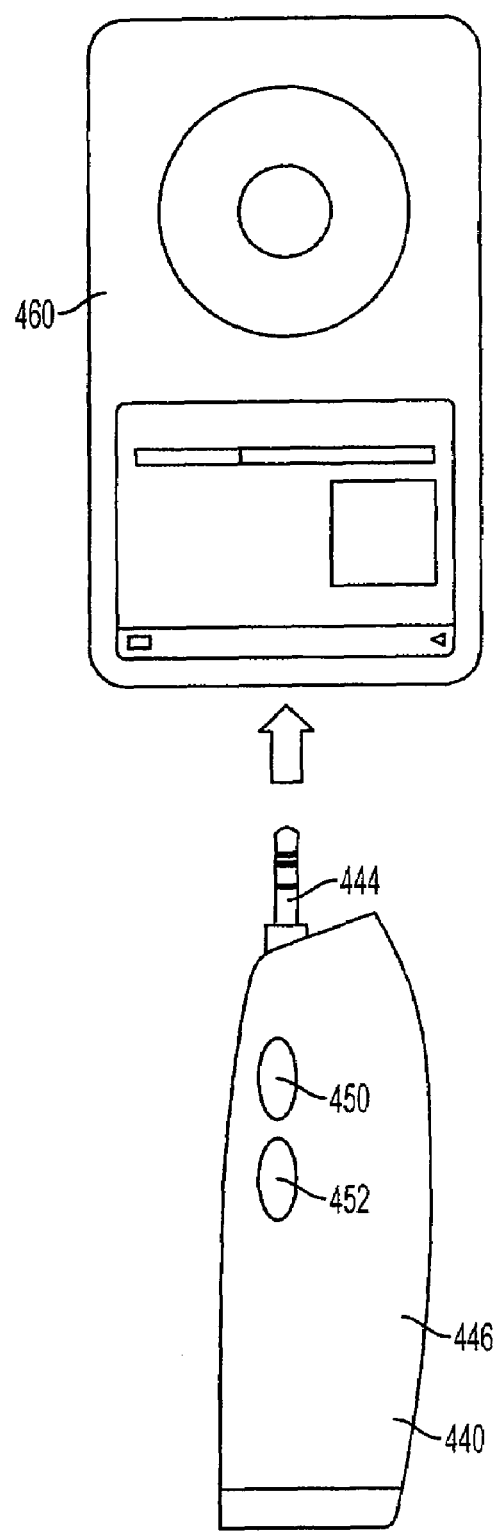
FIG. 12 illustrates the connection of the storage unit of the assembly of FIG. 9 to a signal source.

FIGS. 7-8B illustrate an alternative embodiment of a toothbrush assembly 300 including a plurality of power toothbrushes 320a and 320b removably attached to a base 340 that is mountable to a vertical surface by an attachment such as a locking suction cup 341 or the like. While two toothbrushes 320a, 320b are shown, it will be appreciated that the assembly 300 could operate with any number of toothbrushes as desired. In addition, while the toothbrushes are supported so that the head end and handle end are each free of physical contact with the base 340, it will be appreciated that the base 340 may be configured to allow for other attachment arrangements as desired.

The base 340 further comprises an input 344 for connection to an audio device (not shown), a memory 346 for storing audio signals received via the input 344, and an output in the form of a speaker (not specifically shown) positioned anywhere on the base 340 for transmitting the stored audio signals to the surroundings. The front surface of the base 340 further comprises a record button 350 for recording audio signals to the memory 346, and a play button 352 for playing the recorded audio signals. The play feature may incorporate a timed playback feature as discussed in earlier embodiments. For example, pressing the play button 352 once may result in a two-minute musical interlude, while pressing the play button 352 twice in rapid succession may result in a three-minute musical interlude. A power source 354, such as a battery or the like, is accessible via an access or a door 355 provided on a rear surface of the base 340, to power the record and playback features. Alternatively, the base may plug into an outlet using a supplied cable connection (not shown). Music or other signals are transferred from a signal source (not shown) to the base 340 in a manner similar to that described in FIGS. 4-6.

A wireless port 390 is further provided on the base 340 for communication with similar ports 392, 394 on the toothbrushes 320a, 320b. Such communication can occur using RF (radio frequency), IR (infrared) or other types of signals. A similar port 290 illustrated on the base 240 of FIG. 4 could be used to communicate with the toothbrushes 320a, 320b, or with other similarly-equipped toothbrushes as desired and as described below. In the embodiment of FIGS. 7-8B, the ports 392, 394 communicate to the base 340 when the toothbrushes 320a, 320b are being used, which can then activate the playback of any recorded audio stored in the memory 346. In addition, as shown in FIG. 8B, the toothbrushes 320a, 320b could communicate with each other using the ports 392, 394. In one embodiment, music or the like can only be heard while the user is actually brushing, which provides incentive for the user to brush longer and/or for the recommended period of time that coincides with the duration of the playback. Of course, this can be bypassed if desired through direct use of the play button 352, or in accordance with other control schemes as desired. This system also preserves use of the power source 354, as it is only activated during brushing.

FIGS. 9-12 illustrate an alternative embodiment of a toothbrush assembly 400 including a power toothbrush 420 having a body 425, a removable storage unit 440 that forms a portion of the handle 426, a first power button 428 and a second power button 429. The storage unit 440 further comprises an input 444 for connection to an audio device 460, a memory 446 for storing audio signals received via the input 444, and an output 448 in the form of a speaker positioned on the underside 449 of the unit 440 for transmitting the stored audio signals to the user's surroundings. The storage unit 440 further comprises a record button 450 for recording audio signals to the memory 446, and a play button 452 for playing the recorded audio signals. The play feature may incorporate a timed playback feature as discussed in earlier embodiments. A power source 454, such as a battery or the like, is provided in the storage unit 440 to power the record and playback features as well as any powered element in the toothbrush 420. For example, a vibration generator 422 may be located in the neck 423 to generate vibrations in the head 424, which generator 422 is powered by the power source 454. Alternatively, the storage unit 440 may plug into an outlet using a supplied cable connection (not shown).

Figure 26:
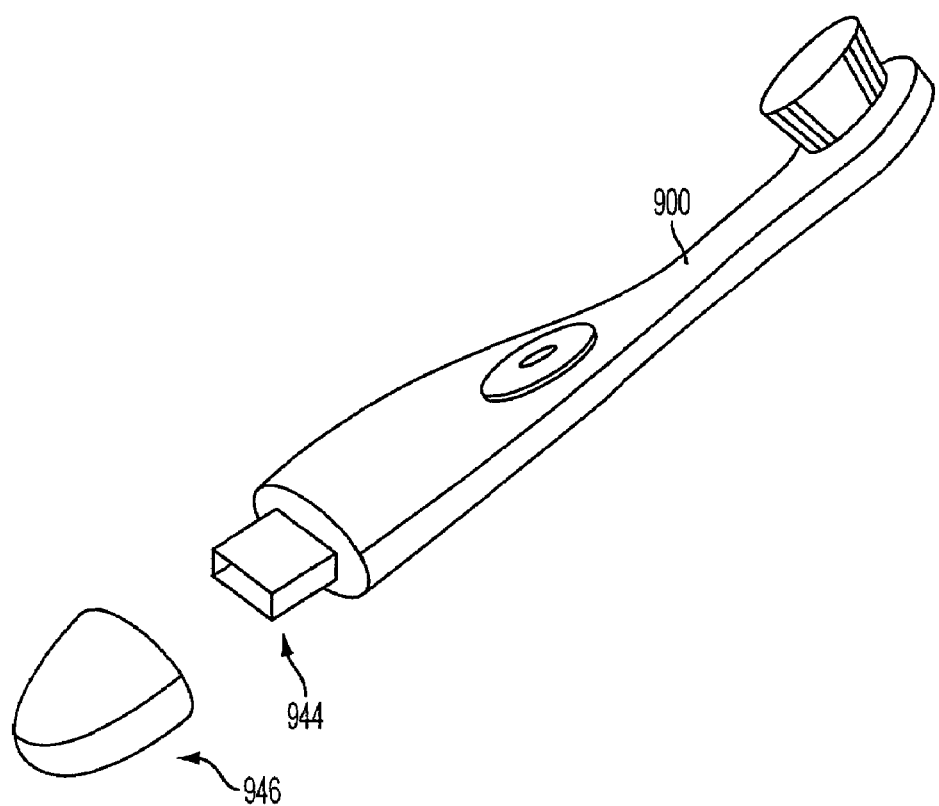
FIG. 26 illustrates an alternative embodiment of an assembly.

In use, the storage unit 440 is removed from the body 425 (FIG. 11) and connected to a signal source 460 by a direct connection with the input 444, which in the embodiment of FIGS. 9-12 is a headphone jack that extends outwardly from the base 440 and that is sealed within the body 425 of the brush when the storage unit 440 is connected thereto. Of course, other input connections are contemplated, such as a USB connector/adapter 944 shown on the toothbrush 900 of FIG. 26, which connector/adapter 944 is covered during use of the toothbrush 900 by a protecting cap 946, and which can function to both communicate with a signal source and a power source such as a recharging base (not shown). In this regard, the physical attachment of the input 444 with the body 425 does not result in signals being transferred from the storage unit 440 to the body 425. The outward extension of the input 444 allows the base 440 to be directly connected or attached to the source 460 at a convenient location. The record and play buttons 450, 452 function in a similar manner as described before, and a timed playback feature could be incorporated as described above.

The first power button 428 is configured to power only the powered element (422 for example) of the brush 420, while the second power button is configured to simultaneously power the powered element 422 and generate a signal output through the speaker 448 for example. If there are no audio signals or the like stored in the memory 446, a user would only use the first power button 428. If it is desired to hear stored music while brushing, the second power button 429 would be used. Other power control schemes are contemplated as desired.

FIGS. 13-15 illustrate an alternative embodiment of a toothbrush assembly 500 including a power toothbrush 520 having a body 525, a removable storage unit 540 that forms a portion of the handle 526, a first power button 528 and a second power button 529. The storage unit 540 is preferably positioned between the head and handle end of the toothbrush 520. The storage unit 540 further comprises an input 544 for connection to an audio device 560, a memory 546 for storing audio signals received via the input 544, and an output 548 in the form of a speaker positioned on the outer surface of the unit 540 for transmitting the stored audio signals to the surroundings. The storage unit 540 further comprises a record button 550 for recording audio signals to the memory 546, and a play button 552 for playing the recorded audio signals. The play feature may incorporate a timed playback feature as discussed in earlier embodiments, while a microphone 545 may be provided for recording ambient sound directly to the memory 546. A first power source 554, such as a battery or the like, is provided in the storage unit 540 to power the record and playback features, while a second power source 555 is provided in the body 525 to power any powered element in the toothbrush 520 as discussed in the embodiment of FIGS. 9-12 above.

Music or other audio signals are transferred from a signal source 560 to the storage unit 540 by a direct connection with the input 544, which in the embodiment of FIGS. 13-16 is a flip-out jack that is movable from a first, storage position recessed within a side surface of the storage unit 540 as shown in FIG. 15, to a second position extending outwardly from the storage unit 540 as shown by the arrow in FIG. 16. The recessed storage position shown in FIG. 15 prevents the input 544 from interfering with a user's grip on the handle 526, while the outward extension of the input 544 allows the storage unit 540 to be directly connected or attached to an audio source 560, such as shown in FIG. 16. The storage unit 540 in the embodiment of FIGS. 13-16 is completely self-contained and, while the toothbrush body 525 includes a recess 542 for accommodating the storage unit 540, the storage unit 540 could function as a musical module apart from the toothbrush body 525 that can be swapped, interchanged or used with other toothbrush bodies or other devices as desired. Furthermore, the portable size of the storage unit 540 makes it particularly suited for easy transport and manipulation In use, the storage unit 540 is removed from the body 525 (FIG. 14) and connected to a signal source 560 with the input 544, after which it is returned to the body 525 for playback during brushing. If the storage unit 540 is electrically connected to the toothbrush 520, the first and second power buttons 528, 529 could function similar to the power buttons 428, 429 of the embodiment of FIGS. 9-12. If the storage unit 540 is not electrically connected to the toothbrush 520, then the first and second power buttons 528, 529 could function simply as "on" and "off" buttons. Other power control schemes are contemplated as desired. In addition, the assembly 500 could be used without connecting to an external source 560. For example, a user can record a message the night before using the microphone input 545, which is played back using the play button 552.

Figure 17:
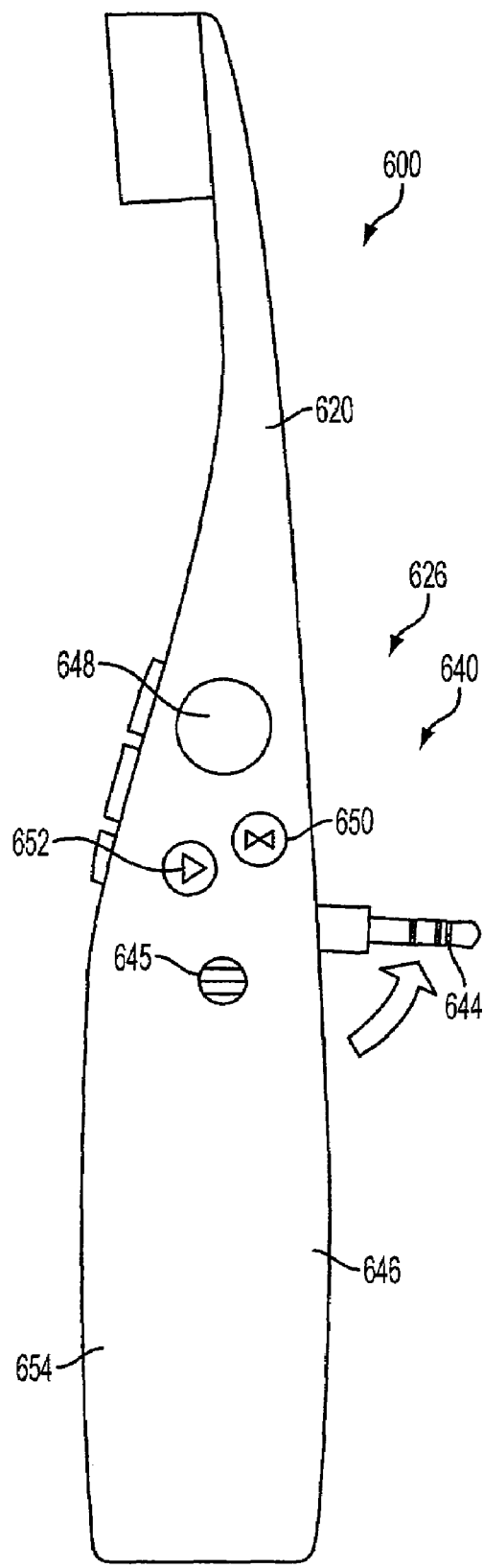
FIG. 17 illustrates an alternative embodiment of a toothbrush assembly of the invention.
Figure 21:
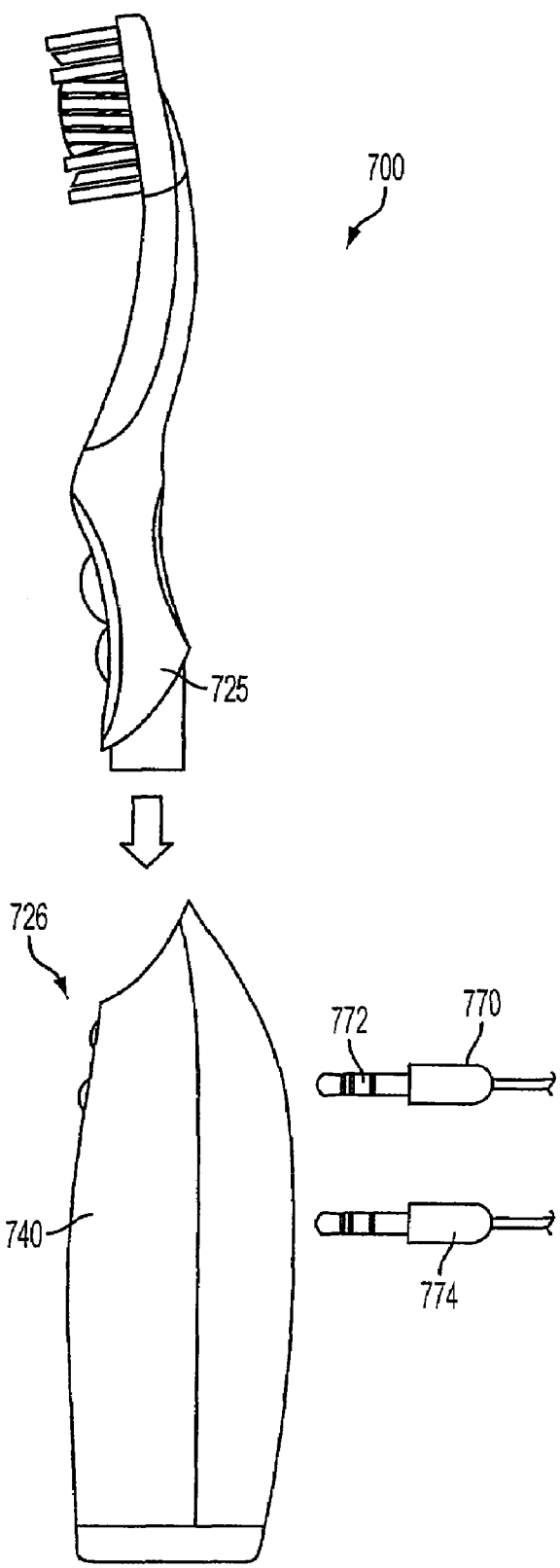
FIG. 21 is an exploded view of the assembly of FIG. 18.

FIG. 17 illustrates an alternative embodiment of a toothbrush assembly 600 including a toothbrush 620 having a body 625 and an integral storage unit 640 that forms a portion of the handle 626. The storage unit 640 further comprises an input 644 for connection to an audio device (not shown), a memory 646 for storing audio signals received via the input 644, and an output 648 in the form of a speaker positioned on the outer surface of the toothbrush 620 for transmitting the stored audio signals to the surroundings. The storage unit 640 further comprises a record button 650 for recording audio signals to the memory 646, and a play button 652 for playing the recorded audio signals. The play feature may incorporate a timed playback feature as discussed in earlier embodiments, while a microphone 645 may be provided for recording ambient sound directly to the memory 646. A power source 654, such as a battery or the like, is provided in the toothbrush 600 to power the record and playback features as well as any powered element in the toothbrush. The input 644 is an integrated flip-out jack that is movable from a first, storage position recessed within a side of the toothbrush 620 to a second position extending outwardly from the toothbrush 620 as shown by the arrow in FIG. 17. In use, the toothbrush 620 is connected to a signal source (not shown) by a direct connection with the input 644. Alternatively, the assembly 600 could be used without connecting to an external source. For example, a user can record a message in the memory 646 using the microphone input 645.

FIGS. 18-21 illustrate an alternative embodiment of a toothbrush assembly 700 including a power toothbrush 720 having a head section 725, a removable storage unit 740 that forms the handle 726, a first power button 728 and a second power button 729. The storage unit 740 further comprises an input 744 for connection to an audio device (not shown), a memory 746 for storing audio signals received via the input 744, and a first output 748a in the form of a speaker positioned on the underside 749 of the unit 740 for transmitting the stored audio signals to the surroundings. The storage unit 740 further comprises a record button 750 for recording audio signals to the memory 746, and a play button 752 for playing the recorded audio signals. The play feature may incorporate a timed playback feature as discussed in earlier embodiments. A power source 754, such as a battery or the like, is provided in the storage unit 740 to power the record and playback features as well as any powered element in the removable toothbrush head section 725. Alternatively, the storage unit 740 may plug into an outlet using a supplied cable connection (not shown).

Music or other audio signals are transferred from a signal source to the storage unit 740 by a wired connection or cable 770 through the use of, for example, a standard headphone jack 772. The user may also discretely listen to the stored audio signals using a headphone connection 774 attached to a second output 748b adjacent the input 744.

FIGS. 22-25 illustrate an alternative embodiment of a toothbrush assembly 800 including a toothbrush 820 having a body 825, a power button 828 and an integral storage unit 840 that forms a portion of the handle 826. The storage unit 840 further comprises an input 844 for connection to an audio device (not shown), a memory 846 for storing audio signals received via the input 844, and a first output 848 in the form of a speaker positioned on the outer surface of the storage unit 840 for transmitting the stored audio signals to the surroundings. The storage unit 840 further comprises a record button 850 for recording audio signals to the memory 846, a play button 852 for playing the recorded audio signals, forward and rewind buttons (collectively as) 851 and a stop button 853. The play feature may incorporate a timed playback feature as discussed in earlier embodiments, while a microphone 845 may be provided for recording ambient sound directly to the memory 846. A power source 854, such as a battery or the like, is provided in the assembly 800 to power the record and playback features as well as any other powered element in the toothbrush 820.

Music or other audio signals are transferred from a signal source (not shown) to the storage unit 840 by a wired connection or cable 870 through the use of, for example, a standard headphone jack 872, to the input 844. Alternatively, the assembly 800 could be used without a connection to an external source. For example, a user can record a message in the memory 846 using the microphone input 845. In addition, the body 825 of the toothbrush 820 can glow, illuminate or otherwise change appearance as an additional output 827 in response to a variety of conditions, such as the type of music being played (i.e., correspond to or emulate the beat of the music being played), the temperature of the user's hand, the time of day (i.e., vibrant color in the morning and soothing color in the evening), etc.

The power button 828 is configured to power any powered element of the brush 820. Such button 828 may also be configured to simultaneously power the powered element and generate a signal output through the speaker 848 for example. Therefore, if there are no audio signals or the like stored in the memory 846, a user would only use the power button 828 to power a powered element provided on the toothbrush 820. If it is desired to hear music while brushing, the power button 828 could be used to automatically activate the playback feature of the storage unit 840. Other power control schemes are contemplated as desired.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A toothbrush assembly comprising: a) a toothbrush; and b) a storage unit comprising an input, a memory for storing audio signals received via the input, and an output for transmitting the stored audio signals; wherein the toothbrush further comprises a body and the storage unit is removably attachable to the toothbrush body; the toothbrush further comprising a head terminating at a first end and a handle terminating at a second end, wherein the storage unit forms the handle of the toothbrush body; and wherein the input extends outwardly from the storage unit.

2. The toothbrush assembly of claim 1, wherein the input is movable from a first position to a second position extending outwardly from the storage unit.

3. The toothbrush assembly of claim 2, wherein the input is configured as a headphone jack.

4. The toothbrush assembly of claim 3, wherein the first position is recessed within the storage unit.

5. The toothbrush assembly of claim 1, wherein the storage unit further comprises a means for recording audio signals to the memory.

6. The toothbrush assembly of claim 5, further comprising a record button on the storage unit for activating the recording means.

7. The toothbrush assembly of claim 6, wherein the storage unit further comprises a means to output the audio signals from the memory.

8. The toothbrush assembly of claim 7, further comprising a playback button on the storage unit for activating the output means.

9. The toothbrush assembly of claim 1, further comprising a wireless connection between the storage unit output and the toothbrush.

10. The toothbrush assembly of claim 9, wherein the toothbrush further comprises a power source, and wherein activation of the power source is communicated to the storage unit via the wireless connection.

11. The toothbrush assembly of claim 10, wherein activation of the power source results in a transmission of the stored audio signals.

12. The toothbrush assembly of claim 9, wherein the wireless connection is a radio frequency connection.

13. The toothbrush assembly of claim 9, wherein the wireless connection is an infrared connection.

14. The toothbrush assembly of claim 13, wherein the storage unit output and the toothbrush each comprises an infrared port.

15. The toothbrush assembly of claim 14, wherein the toothbrush further comprises a power source, and wherein activation of the power source is communicated to the storage unit via the infrared ports.

16. The toothbrush assembly of claim 15, wherein activation of the power source results in a transmission of the stored audio signals.

17. The toothbrush assembly of claim 1, wherein the storage unit is configured to removably receive a plurality of toothbrushes.

18. The toothbrush assembly of claim 1, wherein the storage unit is removably attachable to a vertical surface.

19. The toothbrush assembly of claim 1, wherein the storage unit further comprises a power source.

20. The toothbrush assembly of claim 1, wherein the output is a speaker.

21. The toothbrush assembly of claim 20, wherein the input further comprises a first input and a second input, at least one input being a microphone.

22. The toothbrush assembly of claim 1, wherein the input further comprises a first input and a second input, at least one input being a microphone.

23. The toothbrush assembly of claim 1, wherein at least a portion of the toothbrush is capable of changing appearance.

24. The toothbrush assembly of claim 23, wherein the portion is capable of illumination.

25. The toothbrush assembly of claim 24, wherein the portion exhibits illumination during transmission of the stored audio signals.

26. The toothbrush assembly of claim 1, wherein the storage unit further comprises a means for recording audio signals to the memory.

27. The toothbrush assembly of claim 26, further comprising a record button on the storage unit for activating the recording means.

28. The toothbrush assembly of claim 21, wherein the storage unit further comprises a means to output the audio signals from the memory.

29. The toothbrush assembly of claim 28, further comprising a playback button on the storage unit for activating the output means.

30. The toothbrush assembly of claim 1, the toothbrush further comprising a head terminating at a first end and a handle terminating at a second end, wherein the storage unit is configured to be removably received within a socket spaced from the second end.

31. The toothbrush assembly of claim 30, wherein the storage unit is configured to be removably received in more than one toothbrush.

32. The toothbrush assembly of claim 1, wherein the input is movable from a first position to a second position extending outwardly from the storage unit.

33. The toothbrush assembly of claim 32, wherein the second position extends outwardly from a second side of the storage unit opposite the first side.

34. The toothbrush assembly of claim 33, wherein the input is configured as a headphone jack.

35. The toothbrush assembly of claim 34, wherein the first position is recessed within the storage unit.

36. The toothbrush assembly of claim 1, wherein the storage unit further comprises a power source.

37. The toothbrush assembly of claim 36, wherein the toothbrush body further comprises at least one powered element that is powered by the power source in the storage unit.

38. The toothbrush assembly of claim 36, wherein the toothbrush body further comprises a power source for powering at least one powered element, the toothbrush body power source differing from the storage unit power source.

39. The toothbrush assembly of claim 1, wherein the output is a speaker.

40. The toothbrush assembly of claim 39, wherein the speaker is disposed the bottom of the handle.

41. The toothbrush assembly of claim 1, further comprising a mechanical connection between the input and the toothbrush body.

42. The toothbrush assembly of claim 41, wherein the input is received within a socket in the toothbrush body.

43. The toothbrush assembly of claim 42, wherein the input, when received within the socket, does not transmit audio signals to the toothbrush body.

44. The toothbrush assembly of claim 1, wherein the input is a USB connection.

45. The toothbrush assembly in accordance with claim 1, wherein the storage unit is configured to receive and accommodate any commercially available toothbrush.

46. The toothbrush assembly of claim 9, wherein the wireless connection is a Bluetooth connection.

* * * * *

UNITED STATES PATENT AND TRADEMARK OFFICE
CERTIFICATE OF CORRECTION

| | | |
|---|---|---|
| PATENT NO. | : 7,418,757 B2 | Page 1 of 1 |
| APPLICATION NO. | : 11/413624 | |
| DATED | : September 2, 2008 | |
| INVENTOR(S) | : John J. Gatzemeyer et al. | |

It is certified that error appears in the above-identified patent and that said Letters Patent is hereby corrected as shown below:

On the Title Page, Item (75) in the bibliographic information, the first named inventor should read:
John J. Gatzemeyer Signed and Sealed this
Twenty-fifth Day of January, 2011

David J. Kappos
*Director of the United States Patent and Trademark Office*